US009114143B2

(12) United States Patent
Acebrón Fernández et al.

(10) Patent No.: US 9,114,143 B2
(45) Date of Patent: Aug. 25, 2015

(54) TREATMENT OF VAGINAL ATROPHY IN WOMEN WITH TUMOR PATHOLOGY RISK

(75) Inventors: Álvaro Acebrón Fernández, Alcobendas-Madrid (ES); Dolores Blanco Lousame, Alcobendas-Madrid (ES); Jaime Moscoso Del Prado, Alcobendas-Madrid (ES); Concepción Nieto Magro, Alcobendas-Madrid (ES)

(73) Assignee: ITF RESEARCH PHARMA, S.L.U. (ES)

( * ) Notice: Subject to any disclaimer, the term of this patent is extended or adjusted under 35 U.S.C. 154(b) by 532 days.

(21) Appl. No.: 13/057,775

(22) PCT Filed: Aug. 7, 2009

(86) PCT No.: PCT/EP2009/060307
§ 371 (c)(1),
(2), (4) Date: Apr. 7, 2011

(87) PCT Pub. No.: WO2010/015718
PCT Pub. Date: Feb. 11, 2010

(65) Prior Publication Data
US 2011/0183950 A1    Jul. 28, 2011

(51) Int. Cl.
*A61K 31/56*   (2006.01)
*A61K 31/566*  (2006.01)
*A61K 9/00*    (2006.01)
*A61K 47/32*   (2006.01)
*A61K 47/38*   (2006.01)

(52) U.S. Cl.
CPC ............ *A61K 31/566* (2013.01); *A61K 9/0034* (2013.01); *A61K 47/32* (2013.01); *A61K 47/38* (2013.01)

(58) Field of Classification Search
USPC .......................................... 514/182
See application file for complete search history.

(56) References Cited

U.S. PATENT DOCUMENTS

| 3,159,543 | A | | 12/1964 | Ercoli |
| 4,436,738 | A | * | 3/1984 | Bequette et al. ............. 514/182 |
| 5,340,586 | A | | 8/1994 | Pike et al. |
| 5,719,197 | A | | 2/1998 | Kanios et al. |

(Continued)

FOREIGN PATENT DOCUMENTS

| EP | 0431719 B1 | 11/1994 |
| EP | 0770384 A1 | 5/1997 |

(Continued)

OTHER PUBLICATIONS

Head, Alternative Medicine Review 1998;3(2):101-113.*

(Continued)

*Primary Examiner* — San-Ming Hui
(74) *Attorney, Agent, or Firm* — Tristan A. Fuierer; Moore & Van Allen, PLLC (57) ABSTRACT

The present invention relates to the use of estriol in the preparation of a pharmaceutical formulation for vaginal administration with the capacity to self-limit the absorption of estriol, for the prevention and/or the treatment of urogenital atrophy in women, said women having a high probability of developing an estrogen-dependent tumor or suffering or having suffered from an estrogen-dependent tumor.

23 Claims, 1 Drawing Sheet

(56) References Cited

U.S. PATENT DOCUMENTS

| | | | |
|---|---|---|---|
| 5,894,019 A | 4/1999 | Hesse et al. | |
| 5,942,243 A | 8/1999 | Shah | |
| 2003/0022877 A1 | 1/2003 | Dudley | |
| 2007/0036848 A1 | 2/2007 | Bortz et al. | |
| 2009/0124584 A1 | 5/2009 | Lyle | |

FOREIGN PATENT DOCUMENTS

| | | | |
|---|---|---|---|
| EP | 0818194 A2 | 1/1998 | |
| EP | 0719146 B1 | 12/1998 | |
| EP | 0784466 B1 | 2/2002 | |
| EP | 1325752 A2 | 7/2003 | |
| EP | 1652535 A1 | 5/2006 | |
| EP | 1872775 A1 | 1/2008 | |
| ES | 2171589 | 9/2002 | |
| WO | 8502092 A1 | 5/1985 | |
| WO | 9106289 A1 | 5/1991 | |
| WO | 9629056 A1 | 9/1996 | |
| WO | 9715314 A1 | 5/1997 | |
| WO | 9805303 A1 | 2/1998 | |
| WO | 9820872 A1 | 5/1998 | |
| WO | 9913862 A2 | 3/1999 | |
| WO | 0047144 A1 | 8/2000 | |
| WO | 0050078 A1 | 8/2000 | |
| WO | 0124788 A2 | 4/2001 | |
| WO | 0128515 A1 | 4/2001 | |
| WO | 03037382 A1 | 5/2003 | |
| WO | 2007021805 A2 | 2/2007 | |
| WO | 2007070067 A1 | 6/2007 | |
| WO | 2007085020 | 7/2007 | |
| WO | 2008089405 A1 | 7/2008 | |
| WO | 2009000954 A2 | 12/2008 | |

OTHER PUBLICATIONS

Iosif, C.S., "Effects of protracted administration of estriol on the lower genito urinary tract in postmenopausal women," Arch. Gynecol. Obstet., 1992, pp. 115-120, vol. 251.

Gerbaldo, D, et al, "Endometrial morphology after 12 months of vaginal oestriol therapy in post-menopausal women," Maturitas, 1991, pp. 269-274, vol. 13.

Bottiglione, F. et al., "Transvaginal estriol administration in postmenopausal women: a double blind comparative study of two different doses," Maturitas, Journal of the Climacteric & Postmenopaus, 1995, pp. 227-232, vol. 22.

Dessole, S. et al., "Efficacy of low-dose intravaginal estriol on urogenital aging in postmenopausal women," Menopause: The Journal of the North American Menopause Society, 2004, pp. 49-56, vol. 11.

Foidart, J.M. et al., "Efficacy of sustained-release vaginal oestriol in alleviating urogenital and systemic climacteric complaints," Maturitas, 1991, pp. 99-107, vol. 13.

Samsioe, G., "Cardioprotection by estrogens: mechanisms of action—the lipids," Int. J. Fertil Menopausal Stud.,1994, pp. 43-49, vol. 39, Suppl. 1.

Birkhaeuser, M. et al., "Absorption, Toleranz and klinische Wirkung eines Östriol-Vaginal-Ovulums mit protrahierter Freisetzung des Wirkstoffs," Archives of Gynecology, pp. 228-231, vol. 239.

Palacios, S. et al., "Low-dose, vaginally administered estrogens may enhance local benefits of systemic therpy in the treatment of urogenital atrophy in postmenopausal women on hormone therapy," Maturitas, 2005, pp. 98-104, vol. 50.

Barentsen, R. et al., "Continuous low dose estradiol released from a vaginal ring versus estriol vaginal cream for urogenital atrophy," Eur. J. Obstet. Gynecol. Reprod. Biol., 1997, pp. 73-80, vol. 71.

Pinkerton et al., "Alternatives to the Use of Estrogen in Postmenopausal Women," Endocrine Reviews, 1999, pp. 308-320, vol. 20.

Kicovic, P.M., "The treatment of postmenopausal vaginal atrophy with ovestin vaginal cream or suppositories: clinical, endocrinological and safety aspects," Maturitas, 1980, pp. 275-282, vol. 2.

Katz, F.H., et al., "The effects of estradiol and estriol on plasma levels of cortisol and thyroid hormone-binding globulins and on aldosterone and cortisol secretion rates in man," The Journal of Clinical Investigation, 1967, pp. 1768-1777, vol. 46.

Tamburic, S., et al., "A comparison of different in vitro methods for measuring mucoadhesive performance," European Journal of Pharmaceutics and Biopharmaceutics, 1997, pp. 159-167, vol. 44.

Blanco-Fuente, S. et al., "In-vitro bioadhesion of carbopol hydrogels," Int. J. Pharm., 1997, pp. 169-174, vol. 142.

USP NF, The Official Compendia of Standards, 2002, pp. 2521-2522.

Summary of product characteristics, SPC Ovestin Cream.

Patient Information Leaflet, Ovestin Cream.

Von A. Puck, et al. Die Wirkung des Oestriol aui Coprus uteri, Cervix uteri and Vagina der Frau. Deutsch Medizinische Wochenschrift. 82, p. 1864. 1957.

Beral, Valerie, et al., "Endometrial cancer and hormone-replacement therapy in the Million Women Study," The Lancet, 2005, pp. 1543-1551, vol. 365.

Beral, Valerie, et al., "Ovarian cancer and hormone replacement therapy in the Million Women Study," The Lancet, 2007, pp. 1703-1710, vol. 369.

Holmberty, Lars, et al., "Increased Risk of Recurrence After Hormone Replacement Therapy in Breast Cancer Survivors," J. Natl Cancer Inst., 2008, pp. 475-482, vol. 100.

Ganti, Apar Kishor, et al., "Hormone Replacement Therapy is Associated With Decreased Survival in Women With Lung cancer," Journal of Clinical Oncology, 2006, pp. 59-63, vol. 24.

Haaften et al., Oestrogen concentrations in plasma, endometrium, myometrium and vagina of postmenopausal women, and effects of vaginal oestriol (E3) and oestradiol (E2) applications, J. Steroid Biochem. 1989, vol. 33, pp. 647-653.

Holmgren et al., Vaginal rings for continuous low-dose release of oestradiol in the treatment of urogentical atrophy, Maturitas, 1989, vol. 1989, pp. 55-63.

Lippman et al., Effects of estrone, estradiol, and estriol on hormone-responsive human breast cancer in long-term tissue culture, Cancer Research, 1977, vol. 37, pp. 1901-1907.

Organon Laboratories Limited, Summary of Product Characteristics (SPC) of Ovestin Cream, Sep. 22, 2008.

\* cited by examiner

TREATMENT OF VAGINAL ATROPHY IN WOMEN WITH TUMOR PATHOLOGY RISK

CROSS-REFERENCE TO RELATED APPLICATIONS

This application is filed under the provisions of 35 U.S.C. §371 and claims the priority of International Patent Application No. PCT/EP2009/060307 filed on 7 Aug. 2009 entitled "Treatment of Vaginal Atrophy in Women with Tumor Pathology Risk" in the name of Álvaro ACEBRÓN FERNÁNDEZ, et al., which claims priority of Spanish Patent Application No. P200802384 filed on 7 Aug. 2008, both of which are hereby incorporated by reference herein in their entirety.

The present invention relates to the use of estriol in the preparation of a pharmaceutical formulation for vaginal administration with the capacity to self-limit the absorption of estriol. This formulation is useful in the prevention and/or treatment of urogenital atrophy in women who have high probability of developing an estrogen-dependent tumor.

STATE OF THE ART

Estrogens and other female sex hormones are mainly produced in the ovaries and act throughout life on different tissues and organs. The cells of these organs, among which the breast and the uterus stand out, have receptors for estrogens and for other hormones. Estrogen hormones exert their action by binding to said receptors and starting different physiological or pathological processes. Among other physiological functions, they are responsible for the development and the modifications experienced by the breast and uterus in different life periods (puberty, pregnancy, lactation, menopause). Estrogens can also be involved in pathological processes, stimulating the growth and development of some malignant tumors (for example, breast cancer, endometrial cancer, colon cancer, melanomas) and benign tumors (for example, myomas, hepatic adenomas), both in premenopausal and postmenopausal women.

The medical treatment of the tumors expressing estrogen receptors usually includes the suppression of the production of estrogens or the neutralization of the effects thereof. For example, the hormone therapy of breast carcinomas consists of the administration of drugs blocking the action of hormones stimulating cancer cell proliferation (by modifying their behavior on breast cells or preventing their production). It is given to those patients who are hormone receptor-positive, who constitute 60-70% of the total of the women diagnosed with breast cancer. It has been observed that this type of therapy reduces the recurrences of the disease and prolongs survival. In patients with advanced disease, it reduces the symptoms caused by the tumor, improves the quality of life and causes the remission of the metastasis. It is usually used in combination with other treatments such as surgery, radiotherapy or chemotherapy, in the form of adjuvant or neoadjuvant therapy.

Different types of anti-estrogen therapy for breast cancer can be mentioned by way of example.

Selective Estrogen Receptor Modulators (or SERMs, referred to before as anti-estrogens) selectively inhibit the estrogen receptors of breast cells. Tamoxifen and toremifene are two SERMs currently used in the treatment of breast carcinoma. Raloxifene and other drugs of this family are also in an investigational phase for this indication.

Estrogen receptor inhibitors (or pure estrogen antagonists) bind to said receptors and degrade them, preventing the estrogen from binding to them. The first drug belonging to this subfamily which has been authorized for the treatment of breast cancer is fulvestrant.

Aromatase inhibitors (for example anastrozole, letrozole and exemestane) prevent this enzyme from acting on body fat producing estrogens and, therefore, the blood levels thereof decrease.

Luteinizing hormone-releasing hormone analogs (or LHRH agonists, for example buserelin and goserelin) reduce the levels of estrogens and other sex hormones inhibiting the hypothalamic-hypophyseal-gonadal axis. The effects of this treatment are similar to those which would occur if the ovaries were surgically extirpated, with the advantage that its effects are reversible once the medication is suspended. The surgical extirpation of the ovaries or the elimination of their function by radiotherapy (ovarian ablation) achieves the reduction of the levels of estrogens by eliminating ovarian production but, since it is an irreversible treatment, it is used less and less.

Upon drastically reducing the levels of estrogens, any of these anti-estrogen treatments (for breast cancer or other estrogen-dependent tumors) causes a reversible or irreversible definitive or temporary menopause which can cause a series of undesirable effects in the patient. It can particularly cause urogenital atrophy due to estrogen deficiency which, due to the usual duration of these treatments, can be prolonged for years. In some cases, this atrophy is severe and very negatively affects the quality of life of the patient.

Despite the fact that estrogen therapy is usually very effective in reversing the urogenital atrophy due to hormone deficiency, its use in pre- or postmenopausal patients under anti-estrogen treatment for an estrogen-dependent tumor is not recommended due to the associated risk of stimulating the development of these tumors.

For the same reason, estrogen therapy of urogenital atrophy in postmenopausal women who have a high probability of suffering from an estrogen-dependent tumor is not recommended either.

Urogenital atrophy due to estrogen deficiency does not always require a systemic treatment of the symptoms by means of oral hormone replacement therapy. A preferred alternative is the administration of estrogens by vaginal route. However, this route is not risk-free since locally administered estrogen hormones can be absorbed and pass to the systemic level, increasing the risk of developing (benign or malignant) hormone-dependent tumors, particularly estrogen receptor-positive tumors.

Estriol is one of the estrogens used in the treatment of urogenital atrophy, particularly by vaginal route. Currently marketed vaginal estriol formulations are usually administered in a dose of 0.5 mg/day (500 µg/day) for the first 2-3 weeks of treatment, followed by a dose of 0.5 mg 2 or 3 times/week but, due to the risks that it would entail, their administration in women who have been or are under treatment for an estrogen-dependent tumor or who have a high risk of developing estrogen-dependent tumors is not recommended.

Consequently, the relief of urogenital atrophy due to estrogen deficiency in women who have suffered from or are under treatment for an estrogen-dependent tumor or who have a high probability of developing an estrogen-dependent tumor is an issue that has still not been resolved.

SUMMARY OF THE INVENTION

The inventors of the present invention have surprisingly found that certain vaginal estriol formulations form a system capable of self-limiting the absorption of estriol.

They have seen that, upon starting the treatment with the formulations of the present invention, when the vaginal epithelium is atrophic, there is a low absorption of estriol which is shown in an area under the curve (AUC) of plasma estriol concentration versus time of 1000 pg/ml×h, preferably less than 750 pg/ml×h. Once the repeated administration of these formulations has reversed vaginal atrophy, a fact which, surprisingly, occurs a few days (between 2 and 15 days, particularly between 2 and 10 days, more particularly between 2 and 7 days, even more particularly between 2 and 5 days) after starting the treatment, the absorption of estriol is insignificant and the area under the curve has decreased significantly with respect to the initial one, becoming less than 500 pg/ml×h, preferably less than 250 pg/ml×h. Therefore, the formulations of the present invention can be used without risk or a significantly reduced risk for the treatment or the prevention of urogenital atrophy in women with a high probability of developing estrogen-dependent tumors, women who suffered from an estrogen-dependent tumor or in women who are under treatment for suffering from an estrogen-dependent tumor.

The inventors of the present invention have also surprisingly seen that, upon treating vaginal atrophy with commercially available formulations, the systemic exposure to estriol does not show significant changes throughout the treatment (although at the end the epithelium has become eutrophic) whereas, as already mentioned, upon treatment with the formulations of the present invention the systemic exposure decreases considerably during the treatment.

Consequently, the administration by vaginal route of the estriol formulations of the present invention allows preventing and/or treating urogenital atrophy due to estrogen deficiency while at the same time it achieves preventing or very significantly decreasing the risk associated with estrogen therapy of stimulating the development of estrogen-dependent tumors at systemic level.

A first aspect of the present invention therefore relates to the use of estriol in the preparation of a pharmaceutical formulation for vaginal administration with the capacity to self-limit the absorption of estriol, for the prevention and/or the treatment of urogenital atrophy in women, said women having a high probability of developing an estrogen-dependent tumor or who suffer or have suffered from an estrogen-dependent tumor.

In other words, the present invention refers to a pharmaceutical formulation comprising estriol for vaginal administration with the capacity to self-limit the absorption of estriol, to be used in the prevention and/or treatment of urogenital atrophy in women, said women having a high probability of developing an estrogen-dependent tumor or who suffer or have suffered from an estrogen-dependent tumor.

A second aspect of the present invention relates to a method for preventing or treating the urogenital atrophy in women which comprises vaginally administering an estriol formulation with the capacity to self-limit the absorption of this hormone, said women having a high probability of developing an estrogen-dependent tumor or who suffer or have suffered from an estrogen-dependent tumor.

DETAILED DESCRIPTION OF THE INVENTION

In the context of the present invention, women who have had or are under treatment for an estrogen receptor-positive tumor, or women who have or are exposed to established risk factors: genetic susceptibility (for example, family history of estrogen-dependent cancer, genetic mutations BRCA1 or BRCA2), use/increased production of carcinogenic hormones (for example oral contraceptives, hormone replacement therapy, pregnancy) and lifestyle (alcohol, tobacco, obesity, fat content of the diet, etc.) are considered to be women with a high probability of developing an estrogen-dependent tumor.

An estrogen-dependent tumor includes breast cancer and any other benign, premalignant or malignant tumor pathology expressing estrogen receptors and/or the development of which can be stimulated by estrogens.

Particularly, women who are carrier of genetic mutations BRCA1 or BRCA2, women who are under treatment for or who have a personal history of breast cancer, endometrial cancer, atypical endometrial hyperplasia, preneoplasic lesions, estrogen-dependent melanoma, estrogen-dependent ovarian cancer, estrogen-dependent hepatic tumor, or myomas can benefit from the treatment with the self-limiting formulations of the absorption of estriol of the present invention It is clearly understood that when reference is made to "absorption of striol", it is meant absorption of striol into plasma.

An embodiment of the present invention relates to the use of said self-limiting formulations of the absorption of estriol in the prevention and/or the treatment of urogenital atrophy in women with a high probability of developing an estrogen-dependent tumor.

It also relates to the method of prevention and/or treatment of urogenital atrophy in women with a high probability of developing an estrogen-dependent tumor using the self-limiting formulations of the absorption of estriol of the present invention.

Another embodiment relates to the use of said self-limiting formulations of the absorption of estriol in the prevention and/or the treatment of urogenital atrophy in women who suffer or have suffered from an estrogen-dependent tumor under treatment with any therapy inhibiting the production of estrogens or interfering with the action of the latter on tumor cells.

It also relates to the method of prevention and/or treatment of urogenital atrophy in women who suffer or have suffered from an estrogen-dependent tumor under treatment with any therapy inhibiting the production of estrogens or interfering with the action of the latter on tumor cells using the self-limiting formulations of the absorption of estriol of the present invention.

A preferred embodiment relates to the use of said formulations in women with an estrogen-dependent tumor, for example estrogen receptor-positive breast cancer, under treatment with selective estrogen receptor modulators.

Another preferred embodiment relates to the use of said formulations in women with an estrogen-dependent tumor, for example with estrogen receptor-positive breast cancer, under treatment with estrogen receptor inhibitors.

Another more preferred embodiment relates to the use of said formulations in women with an estrogen-dependent tumor, for example with estrogen receptor-positive breast cancer, under treatment with aromatase inhibitors.

Another preferred embodiment relates to the use of said formulations in women with an estrogen-dependent tumor, for example with estrogen receptor-positive breast cancer, under treatment with luteinizing hormone-releasing hormone analogs.

Another preferred embodiment relates to the use of said formulations in women with an estrogen-dependent tumor, particularly with estrogen receptor-positive breast cancer, who have undergone an ovarian ablation.

Another embodiment also relates to a method for preventing the risk of developing hormone-dependent tumors at systemic level associated with estrogen therapy which comprises vaginally administering an estriol formulation characterized by the capacity to self-limit the absorption of this hormone.

As already mentioned, the pharmaceutical formulations useful in the method of treatment of the present invention are those which form a self-limiting system of the absorption of estriol. In the context of the present invention, a formulation with the capacity of self-limit the absorption of estriol is that one which provides a low absorption of hormone (estriol plasma peaks less than 150 pg/ml, preferably less than 125 pg/ml)) when the vaginal mucosa is atrophic and insignificant absorption (which is shown in plasma estriol peaks close to baseline physiological values) once the atrophy has been reversed by the local action of estriol.

In particular, the pharmaceutical formulation can be any which, upon being vaginally administered, provides estriol plasma peaks less than 50 pg/ml, preferably less than 30 pg/ml, more preferably less than 25 pg/ml, even more preferably less than or equal to 20 pg/ml, after the repeated once daily administration for a time between 1 and 4 weeks, more particularly between 2 and 3 weeks and after this period if the administration continues.

According to a preferred embodiment, the pharmaceutical formulation of the present invention can be any which enables a significant decrease of the systemic exposure to estriol (quantified using the AUC of plasma estriol concentrations as a function of time) after its repeated daily administration for several days, once the vaginal atrophy has been reversed. In particular, it is any which provides an AUC less than 1000 pg/ml×h, preferably less than 750 pg/ml×h, more preferably less than 600 pg/ml×h, at the start of the treatment, more particularly in the first day of the treatment, and an AUC less than 750 pg/ml×h, preferably less than 500 pg/ml×h, more preferably less than 300 pg/ml×h, even more preferably less than 250 pg/ml×h, after the repeated once daily administration for a time between 1 and 4 weeks, particularly between 2 and 3 weeks, and after this period if the administration continues.

In an especially preferred embodiment, the pharmaceutical formulation of the present invention can be any which enables an almost insignificant systemic exposure once the urogenital atrophy has been reversed. It is particularly any which provides an AUC less than or equal to 150 pg/ml×h after the repeated once daily administration for a time between 1 and 4 weeks, preferably between 2 and 3 weeks, and after this period if the administration continues.

The pharmaceutical formulation can be, for example, in solid (pessaries, tablets, etc.), semisolid (gels, creams, etc.), liquid or foam form. And it can contain any of the excipients known by a person skilled in the art. According to a preferred embodiment, the pharmaceutical compositions of the present invention are semisolid formulations for example gels, cream gels or creams.

In a preferred embodiment, they are mucoadhesive gels, cream gels or creams containing at least one bioadhesive polymer (gelling agent and/or thickener) and an amount of estriol such that it allows administering less than 0.5 mg/day.

In a more preferred embodiment, the mucoadhesive formulations of the present invention contain at least two bioadhesive polymers and an amount of estriol such that it allows administering less than 0.3 mg/day, preferably less than 0.1 mg/day, still more preferably between 0.07 and 0.002 mg/day. For example, the formulations can contain estriol in an amount less than or equal to 0.03% by weight, preferably less than or equal to 0.01% by weight, more preferably between 0.007 and 0.0002% by weight, even more preferably between 0.005 and 0.001% by weight of the formulation.

The bioadhesive polymers useful for the formulations of the present invention are chosen from cellulose polymers, natural gums, sodium alginate, polyoxyethylenes, acrylic homo or copolymers, and mixtures thereof.

The cellulose polymers can be selected from methylcellulose, carboxymethylcellulose sodium, hydroxyethyl cellulose, hydroxypropyl cellulose and hydroxypropyl methylcellulose. The natural gums can be chosen, for example, from guar gum, karaya gum, xanthan gum and veegum. The acrylic polymers are preferably selected from polymers of the type of acrylic acid crosslinked with divinyl glycol (marketed under the trademark Noveon® AA-1 Polycarbophil) and polymers derived from acrylic acid crosslinked with allyl sucrose or allyl pentaerythritol designated as carbomer type polymers (marketed under the trademark Carbopol®).

Carbomer is the generic name adopted by a number of agencies, including the United States Pharmacopeia-National Formulary (USP-NF), United States Adopted Names Council (USAN) and the European Pharmacopoeia, for defining a various types of high molecular crosslinked acrylic acid-based polymers, which are marketed as Carbopol® polymers. U.S. Pat. Nos. 2,798,053, 4,267,103, 5,349,030, 4,996,274, 4,509,949, 5,373,044 describe these polyacrylic acid polymers, including the Carbopol® type, which are incorporated herein by reference. The "Handbook of Pharmaceutical Excipients", 2006, also describe the Carbopol® type polymers under the title "Carbomer", being this monograph also included herein by reference.

Carbomer type polymers and Polycarbophil polymer are manufactured by cross-linking process. Depending upon the degree of cross-linking and manufacturing conditions, various grades of Carbopol are available. Carbopol® 934 P is cross-linked with allyl sucrose and is polymerized in solvent benzene. Carbopol 5984 EP is cross-linked with allyl sucrose and polimerized in ethyl acetate and cyclohexane. Carbopol® 71G, 971 P, 974 P are cross-linked with allyl pentaerythritol and polymerized in ethyl acetate. Carbopol® 980 and 981 are cross-linked with allyl penta-erythritol and polymerized in a cosolvent mixture of ethyl acetate and cyclohexane. Polycarbophil is cross-linked polymer in divinyl glycol and polymerized in solvent benzene or ethylacetate. All the polymers fabricated in ethyl acetate are neutralized by 1-3% potassium hydroxide.

Though Carbopol® 971 P and Carbopol® 974 P are manufactured by same process under similar conditions, the difference between them is that Carbopol® 971 P (USP29/NF24 Carbomer Homopolymer Type A) has slightly lower level of cross-linking agent than Carbopol® 974 P (USP29/NF24 Carbomer Homopolymer Type B). As a result, Carbopol® 971 P NF has a viscosity between 4000 and 11000 cP (measured in Brookfield RTV viscometer at 20 rpm, 25° C., in a 0.5% by weight mucilage, neutralized to pH 7.3-78), while Carbopol® 974 P NF has a viscosity between 29400 and 39400 cP (measured in Brookfield RTV viscometer at 20 rpm, 25° C., in a 0.5% by weight mucilage, neutralized to pH 7.3-7.8). For similar reasons, Carbopol® 981 NF has a viscosity between 4,000 and 10,000 cP (measured in Brookfield RTV viscometer at 20 rpm, 25° C., in a 0.5% by weight mucilage, neutralized to pH 7.3-78), while Carbopol® 980 NF has a viscosity between 40,000 and 60,000 cP (measured in Brookfield RTV viscometer at 20 rpm, 25° C., in a 0.5% by weight mucilage, neutralized to pH 7.3-7.8).

In an even more preferred embodiment, the mucoadhesive formulations used in the methods of the present invention contain at least one carbomer type polymer selected from polymers of acrylic acid crosslinked with allyl ethers of pentaerythritol, at least one polyacrylic acid crosslinked with divinylglycol and estriol in an amount such that it allows administering less than or equal to 0.1 mg/day.

The carbomer type polymer is preferably chosen from those whose synthesis does not require the use of benzene as solvent, such as Carbopol® 71G NF, Carbopol® 971P NF, Carbopol® 974P NF, Carbopol® 980 NF, Carbopol® 981 NF and Carbopol® 5984 EP. More preferably, the carbomer type polymer is chosen from those polymerized in ethyl acetate or in a mixture of ethyl acetate and cyclohexane. Even more preferably, the carbomer type polymer is chosen from those polymerized in ethyl acetate or in a mixture of ethyl acetate and cyclohexane and with a viscosity between 4,000 and 11,000 cP.

In a particularly preferred embodiment, the formulations contain at least two bioadhesive polymers, one is a carbomer type homopolymer selected from Carbopol® 971P NF and Carbopol® 981 NF and the other is Noveon® AA-1 Polycarbophil, and an amount of estriol less than or equal to 0.03% by weight of the formulation.

In a more preferred embodiment the formulations contain at least Noveon® AA-1 Polycarbophil and Carbopol® 971P NF, and an amount of estriol less than or equal to 0.03% by weight of the formulation.

Each of the polymers is incorporated in the amount necessary to provide the formulation with the physicochemical and organoleptic properties suitable for vaginal administration. In the case of acrylic polymers, the amount will be between 0.05 and 5% by weight of the formulation, preferably between 0.1 and 2%, more preferably between 0.25 and 1.5%.

The formulation can further contain other pharmaceutically acceptable excipients such as moisturizing agents, wetting agents, solubilizing agents, emulsifiers, preservatives, fatty or lipophilic substances, etc. in amounts known by a person skilled in the art.

Said formulations can be prepared by processes known by a person skilled in the art.

The formulations used in the methods of the present invention are preferably administered in an amount sufficient to form a layer over the entire vaginal surface and to obtain an effective and safe dosage regimen. For example, in the case of semisolid formulations, usually between 1 to 5 grams.

The devices which can be used for the administration of the semisolid formulations used in the method of the present invention are any of those one-dose or single-dose applicators known in the state of the art, for example an applicator with a plunger or with a bellows.

The dose of estriol to be administered to the patients treated with the methods of the present invention will be less than 0.5 mg/day, preferably less than 0.3 mg/day, more preferably less than 0.1 mg/day.

In a particular embodiment of the present invention, estriol is administered in doses between 0.002 and 0.07 mg/day (2 and 70 µg/day), preferably between 0.002 and 0.05 mg/day (2 and 50 µg/day), more preferably between 0.01 and 0.05 mg/day (10 and 50 µg/day), especially preferably between 0.02 and 0.05 mg/day (20 and 50 µg/day), for the prevention and/or the treatment of urogenital atrophy due to estrogen deficiency in women with a high probability of developing an estrogen-dependent tumor, particularly an estrogen receptor-positive cancer.

In another particular embodiment, estriol is administered in doses between 0.002 and 0.07 mg/day (2 and 70 µg/day), preferably between 0.002 and 0.05 mg/day (2 and 50 µg/day), more preferably between 0.01 and 0.05 mg/day (10 and 50 µg/day), especially preferably between 0.02 and 0.05 mg/day (20 and 50 µg/day), for the treatment of urogenital atrophy due to estrogen deficiency in women who have suffered or suffer from an estrogen-dependent tumor under treatment with any therapy inhibiting the production of estrogens or interfering with the action of the latter on tumor cells.

Given the high safety of the formulations used in the method of the present invention, the treatment or the prevention of the vaginal atrophy can be performed simultaneously to the treatment or the prevention of the hormone-dependent tumor.

The duration of the treatment and/or prevention of urogenital atrophy and the administration regimen of the present formulations will depend on the condition of the patient, the response to the treatment and the concomitant therapy. For example, a dose between 0.002 and 0.07 mg, preferably between 0.01 and 0.05 mg a day for 2 or 3 weeks will be administered, and this will be continued with a dose between 0.002 and 0.07 mg, preferably between 0.01 and 0.05 mg twice a week for the time necessary to maintain the trophic state of the vaginal mucosa, without interrupting the treatment. Alternatively, a dose between 0.002 and 0.07 mg, preferably between 0.01 and 0.05 mg a day for 2 or 3 weeks will be administered, and this will be continued with a dose between 0.002 and 0.07 mg, preferably between 0.01 and 0.05 mg twice a week for a few weeks, for example between 6 and 10 weeks, thus interrupting the treatment until the symptoms appear again. Alternatively, given the high safety of the formulations used in the methods of the present invention, its administration could be continued with a daily dose, or a twice weekly dose, between 0.002 and 0.07 mg, preferably between 0.01 and 0.05 mg, for more than 3 weeks, or more than 10 weeks, respectively.

An illustrative example of the invention is described below. In no case should it be considered as limiting for the interpretation of the claims.

Assay

Comparative pharmacokinetics and efficacy of two estriol formulations of the invention versus a commercial estriol formulation (Ovestinon® cream, Organon) in postmenopausal women Description The assayed formulations were two vaginal gels based on estriol T1 (0.002% ITFE) and T2 (0.005% ITFE) with the following composition:

|  | Compound | amount | amount |
|---|---|---|---|
| Active ingredient | Estriol | 0.002% | 0.005% |
| Excipients | Carbopol ® 971 (0.5%) | 2% | 2% |
|  | Polycarbophil Noveon ® AA-1 (1.5%) | | |
|  | Glycerin | 10% | 10% |
|  | Methylparaben | 0.16% | 0.16% |
|  | Propylparaben | 0.02% | 0.02% |
|  | Sodium hydroxide | q.s. pH = 4.5 | q.s. pH = 4.5 |
|  | Water | q.s. 100% | q.s. 100% |

These formulations were compared with a placebo formulation, without estriol, and a commercially available formulation (Ovestinon® cream, with 0.1% estriol).

Seventy postmenopausal women with vaginal atrophy participated in the assay, who were randomly distributed in four groups, 3 with 20 patients each and one with 10 patients:

The women received daily treatment for 21 consecutive days. 1 g of gel a day by vaginal route was administered to each patient of Groups B, C and D and 0.5 g of cream a day by vaginal route were administered to each patient of Group A.

| | |
|---|---|
| Group A: treated with Ovestinon (Reference "R") | (n = 20) |
| Group B: treated with 0.005% ITFE | (n = 20) |
| Group C: treated with 0.002% ITFE | (n = 20) |
| Group D: treated with 0% ITFE (Placebo "P") | (n = 10) |

The pharmacokinetic study was conducted in a subgroup of 42 women formed by 12 patients of each of the groups which were receiving active treatment (n=12 Group A, n=12 B, n=12 C).

The day before starting the treatment, the patients were subjected to a gynecological evaluation and to a cervical-vaginal cytology.

On the first day of treatment, the formulation corresponding to the assigned group was vaginally administered to all the patients and blood samples at time 0 (pre-dose), 0.5, 1, 2, 3, 4, 6, 8, 12 and 24 h (post-dose) were only extracted from the 42 volunteers of the pharmacokinetic study.

On the second day, the administration to all the patients was repeated and blood was only extracted from the 42 volunteers.

On days 3 to 20 of the treatment, the corresponding formulation was vaginally administered daily to all the patients. On days 7 and 14, subjective efficacy and tolerability immediately before the administration were evaluated.

On day 21, all the patients received the last dose of the treatment and blood samples at time 0 (pre-dose), 0.5, 1, 2, 3, 4, 6, 8, 12 and 24 h (post-dose) were only extracted from the 42 volunteers of the pharmacokinetic study. Local tolerability was evaluated 12 hours after the administration.

On day 22, all the patients were subjected to a gynecological evaluation and to a cervical-vaginal cytology and blood samples at the aforementioned times were only extracted from the 42 volunteers.

Assessment of the Effect on Vaginal Atrophy

The vaginal smears extracted during the gynecological evaluation of days 0 and 22 were fixed with a water-soluble solution for cytodiagnosis (ethanol/methanol EDTA) and stained according to the Papanicolaou technique for the qualitative evaluation of the cytological state and the count of superficial cells (SC), intermediate cells (IC) and parabasal cells (PC), which will be used in the subsequent determination of the maturation index (MI) and of the maturation value (MV).

The Maturation Value (MV) is calculated from the Maturation Index (MI) as follows = $0.2 \times \%$ of parabasal cells + $0.6 \times \%$ of intermediate cells + $1.0 \times \%$ of superficial cells.

The data of the qualitative and quantitative assessments (MI and MV) are shown in Tables I, II and III

TABLE I

Frequency of the cytological pattern on day 0 (baseline level) and on day 22 (after the administration of formulations T1, T2, R or placebo).

| Cytological pattern | T1 Day 0 | T1 Day 22 | T2 Day 0 | T2 Day 22 | R Day 0 | R Day 22 | P Day 0 | P Day 22 |
|---|---|---|---|---|---|---|---|---|
| Atrophic | 7 | 1 | 7 | 0 | 7 | 0 | 2 | 2 |
| Slightly proliferative | 5 | 5 | 4 | 5 | 5 | 3 | 4 | 4 |
| Proliferative | 1 | 2 | 0 | 1 | 0 | 3 | 0 | 0 |
| Highly proliferative | 0 | 5 | 0 | 5 | 0 | 6 | 0 | 0 |
| Total | 13 | 13 | 11 | 11 | 12 | 12 | 6 | 6 |

TABLE II

Maturation index (MI) based on the differential count of superficial cells (SC), intermediate cells (IC) and parabasal cells (PC) on days 0 and 22 and difference with the baseline levels ($\Delta$SC, $\Delta$IC and $\Delta$PC) after the administration of formulations T1, T2, R and P.

| | SCs/300: Mean value ± SD | | | ICs/300: Mean value ± SD | | |
|---|---|---|---|---|---|---|
| | Day 0 | Day 22 | $\Delta$SC | Day 0 | Day 22 | $\Delta$IC |
| T1 | 12.92 ± 23.67 | 110.08 ± 79.80 | 97.15 ± 79.44 | 177.00 ± 117.11 | 174.00 ± 72.36 | −3.00 ± 107.71 |
| T2 | 10.75 ± 12.17 | 111.25 ± 71.45 | 100.50 ± 76.84 | 207.00 ± 105.51 | 187.75 ± 71.25 | −19.25 ± 71.38 |
| R | 9.50 ± 14.00 | 150.75 ± 73.55 | 141.25 ± 66.39 | 209.00 ± 95.82 | 149.25 ± 73.55 | 59.75 ± 126.06 |
| P | 15.50 ± 14.63 | 23.00 ± 18.26 | 7.50 ± 4.55 | 198.00 ± 123.90 | 206.50 ± 94.21 | 8.50 ± 34.12 |

| | PCs/300: Mean value ± SD | | |
|---|---|---|---|
| | Day 0 | Day 22 | $\Delta$PC |
| T1 | 110.08 ± 126.83 | 15.92 ± 43.98 | −94.15 ± 118.65 |
| T2 | 82.25 ± 112.73 | 1.00 ± 3.46 | −81.25 ± 111.46 |
| R | 81.50 ± 102.24 | 0.00 ± 0.00 | −81.50 ± 102.24 |
| P | 86.50 ± 135.48 | 70.50 ± 109.2 | −16.00 ± 32.40 |

TABLE III

Maturation value (MV) on days 0 and 22 and difference
with the baseline level (ΔMV) after the administration
of formulations T1, T2, R and P.

| | MV: Mean value ± SD | | |
|---|---|---|---|
| Treatment | Day 0 | Day 22 | ΔMV |
| T1 | 47.12 ± 18.73 | 72.51 ± 14.34 | 25.38 ± 22.85 |
| T2 | 50.13 ± 15.89 | 74.70 ± 9.57 | 24.57 ± 23.43 |
| R | 50.50 ± 14.47 | 80.08 ± 9.84 | 29.58 ± 15.63 |
| P | 50.53 ± 19.68 | 53.67 ± 16.68 | 3.13 ± 4.17 |

It can therefore be concluded that the method of treatment of the present invention is effective in reversing vaginal atrophy.

Assessment of the Plasma Levels of Estriol

The plasma estriol concentration was determined by liquid chromatography/mass spectrometry (LC-MS/MS) in the blood samples extracted at time 0 (pre-dose), 0.5, 1, 2, 3, 4, 6, 8, 12 and 24 h (post-dose) on days 0, 1, 21 and 22 from the 42 volunteer patients.

Figure 1:
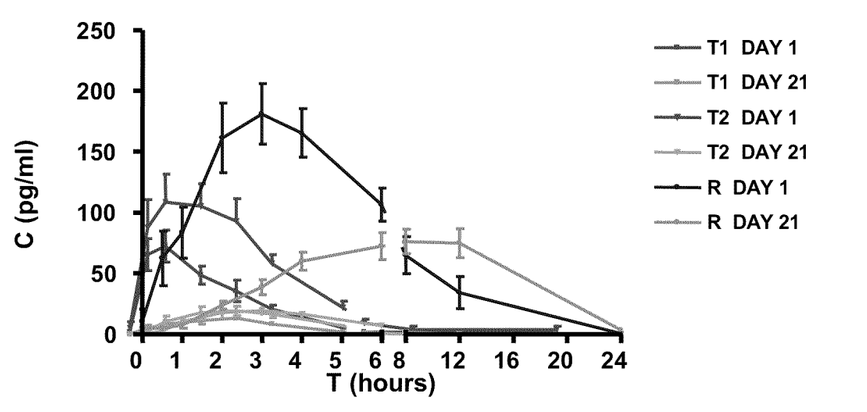
FIG. 1. Plasma estriol concentrations as a function of time.

The plasma levels obtained on the first day of treatment and on day 21 are shown in Tables IV and VI and in Graph 1.

The pharmacokinetic parameters calculated from these values are shown in Tables V and VII.

TABLE IV

Plasma levels of estriol after the administration of
a single dose of formulations T1, T2 and R. Day 1

| | Plasma levels of estriol: Mean value ± SD (pg/mL) | | |
|---|---|---|---|
| Time (h) | T1 | T2 | R |
| 0 | 1.48 ± 3.46 | 5.17 ± 17.90 | 10.33 ± 35.80 |
| 0.5 | 65.24 ± 45.54 | 87.59 ± 79.24 | 62.45 ± 78.01 |
| 1 | 72.43 ± 45.46 | 108.57 ± 79.76 | 83.36 ± 72.14 |
| 2 | 48.63 ± 25.79 | 105.20 ± 64.12 | 161.40 ± 98.58 |
| 3 | 35.53 ± 30.05 | 92.81 ± 64.15 | 180.88 ± 85.98 |
| 4 | 20.46 ± 12.27 | 57.78 ± 25.77 | 165.34 ± 68.88 |
| 6 | 5.57 ± 6.30 | 21.82 ± 17.83 | 106.43 ± 46.98 |
| 8 | 1.56 ± 3.67 | 9.02 ± 10.82 | 65.02 ± 52.91 |
| 12 | 1.65 ± 3.86 | 3.86 ± 10.02 | 34.20 ± 45.02 |
| 24 | 1.89 ± 5.12 | 3.85 ± 9.25 | 0.56 ± 1.92 |

TABLE V

Pharmacokinetic parameters (±SD) of estriol after the administration
of a daily single dose of formulations T1, T2 and R. Day 1

| | $C_{max}$ (pg/mL) Corrected dose | $T_{max}$ (h) | $AUC_{0-t}$ (pg/mL × h) Corrected dose | $AUC_{0-\infty}$ (pg/mL × h) Corrected dose | $t_{1/2}$ (h) | MRT (h) |
|---|---|---|---|---|---|---|
| T1 | 60.57 ± 27. | 1.29 ± 0 | 171.65 ± 80 | 194.29 ± 73 | 1.59± | 3.99± |
| T2 | 106.40 ± 63 | 2.38 ± 1 | 406.75 ± 19 | 461.53 ± 17 | 1.65± | 4.57± |
| R | 210.06 ± 82 | 3.04 ± 1 | 1221.97 ± 5 | 1431.21 ± 8 | 2.52± | 5.79± |

TABLE VI

Plasma levels of estriol after the administration
of daily doses of formulations T1, T2 and R. Day 21

| | Plasma levels of estriol: Mean value ± SD (pg/mL) | | |
|---|---|---|---|
| Time (h) | T1 | T2 | R |
| 0 | BLQL | BLQL | 4.98 ± 6.45 |
| 0.5 | 5.18 ± 8.07 | 2.48 ± 6.14 | 4.92 ± 6.54 |
| 1 | 8.40 ± 10.29 | 10.56 ± 14.39 | 7.33 ± 8.28 |
| 2 | 11.20 ± 9.92 | 17.79 ± 17.01 | 23.94 ± 11.60 |
| 3 | 13.00 ± 7.25 | 19.32 ± 13.88 | 38.58 ± 21.40 |
| 4 | 8.47 ± 6.28 | 16.30 ± 9.16 | 60.08 ± 25.51 |
| 6 | 1.63 ± 4.21 | 7.28 ± 5.62 | 72.36 ± 39.18 |
| 8 | 0.87 ± 3.00 | 1.85 ± 3.43 | 76.17 ± 34.78 |
| 12 | BLQL | BLQL | 74.81 ± 41.68 |
| 24 | BLQL | BLQL | 3.47 ± 7.40 |

BLQL = below the lower quantification limit (5 pg/mL)

TABLE VII

Pharmacokinetic parameters (±SD) of estriol after the administration
of daily doses of formulations T1, T2 and R. Day 21

| | $C_{ssmax}$ (pg/mL) Corrected dose | $T_{ssmax}$ (h) | $C_{ssmin}$ (pg/mL) | $AUC_{ssmax}$ (pg/mL × h) Corrected dose |
|---|---|---|---|---|
| T1 | 13.77 ± 8.03 | 2.17 ± 0.94 | 0.0 ± 0.0 | 36.33 ± 30.52 |
| T2 | 22.80 ± 15.78 | 3.25 ± 1.14 | 0.0 ± 0.0 | 73.71 ± 46.86 |
| R | 89.95 ± 38.55 | 7.67 ± 3.06 | 2.97 ± 5.49 | 800.11 ± 363.51 |

It can therefore be concluded that the safety profile of the formulations of the present invention is highly favorable since the systemic exposure to estriol after repeated administration is almost insignificant (extremely low). Additionally, the systemic exposure is significantly lower than that occurring after the administration of the reference product.

In addition, although the systemic exposure to estriol is significantly lower, the formulations of the present invention cause a similar increase of the maturation value on day 22 compared to day 0, indicating an effect similar to that of the reference product in vaginal mucosa.

The invention claimed is:

1. A method of prevention and/or treatment of urogenital atrophy due to estrogen deficiency in women which comprises vaginally administering a pharmaceutical estriol formulation capable of self-limiting absorption of estriol, wherein said women suffer or have suffered from an estrogen-dependent tumor or are carrier of genetic mutations BRCA1 or BRCA2 and wherein the pharmaceutical formulation is administered in a dose of estriol less than or equal to 0.3 mg/day.

2. The method according to claim 1, wherein the pharmaceutical formulation provides an area under the curve of plasma estriol concentration as a function of time of less than 500 pg/ml×h after the administration of repeated once daily doses for a time between 1 and 4 weeks.

3. The method according to claim 2, wherein the pharmaceutical formulation provides an area under the curve of less than 300 pg/ml×h.

4. The method according to claim 2, wherein the pharmaceutical formulation provides an area under the curve of less than or equal to 150 pg/ml×h after the administration of repeated once daily doses for a time between 2 and 3 weeks.

5. The method according to claim 1, wherein the pharmaceutical formulation provides plasma levels of estriol of less than 50 pg/ml after the repeated once daily administration for a time between 1 and 4 weeks.

6. The method according to claim 5, wherein the pharmaceutical formulation provides plasma levels of estriol of less than 25 pg/ml after the repeated once daily administration for a time between 2 and 3 weeks.

7. The method according to claim 1, wherein the estriol plasma peak is less than 150 pg/ml when the vaginal epithelium is atrophic and the absorption of estriol becomes insignificant once repeated administration of the pharmaceutical formulation has reversed the vaginal atrophy.

8. The method of estriol according to claim 7, wherein the area under the curve of plasma estriol concentration versus time is less than 1000 pg/ml×h when the vaginal epithelium is atrophic, and less than 500 pg/ml×h once vaginal atrophy has been reversed.

9. The method of estriol according to claim 8, wherein the area under the curve of plasma estriol concentration versus time is less than 750 pg/ml×h when the vaginal epithelium is atrophic, and less than 250 pg/ml×h once vaginal atrophy has been reversed.

10. The method according to claim 9, wherein vaginal atrophy is reversed between 2 and 10 days after the beginning of the treatment.

11. The method according to claim 1 for the prevention or the treatment of urogenital atrophy due to estrogen deficiency in women who are carrier of genetic mutations BRCA1 or BRCA2.

12. The method according to claim 1 for the prevention or the treatment of urogenital atrophy due to estrogen deficiency in women who suffer or have suffered from an estrogen-dependent tumor selected from breast cancer, endometrial cancer, atypical endometrial hyperplasia, preneoplasic lesions, estrogen-dependent melanoma, estrogen-dependent ovarian cancer, estrogen-dependent haptic tumor, or myomas.

13. The method according to claim 12, wherein the women have undergone an ovarian ablation or are under treatment with at least one drug inhibiting the production or interfering with the action of estrogens in the organisms, wherein the drug is selected from the group consisting of a selective estrogen receptor modulator, an estrogen receptor inhibitor, an aromatase inhibitor, and a luteinizing hormone-releasing hormone analog.

14. The method according to claim 1, wherein the dose of estriol is between 0.002 and 0.07 mg/day.

15. The method according to claim 1, wherein the pharmaceutical formulation is a mucoadhesive gel, cream gels or cream containing at least one bioadhesive polymer.

16. The method according to claim 15, wherein said bioadhesive polymer is selected from the group consisting of cellulose polymers, natural gums, sodium alginate, polyoxyethylenes, acrylic polymers and mixtures thereof.

17. The method according to claim 16, wherein said bioadhesive polymer is selected from the group consisting of methylcellulose, carboxymethylcellulose sodium (CMC), hydroxyethyl cellulose (HEC), hydroxypropyl cellulose (HPC) and hydroxypropyl methylcellulose (HPMC).

18. The method according to claim 16, wherein said bioadhesive polymer is selected from the group consisting of polymers of the type of acrylic acid crosslinked with divinyl glycol and polymers derived from acrylic acid crosslinked with allyl sucrose or allyl pentaerythritol.

19. The method according to claim 18, wherein the amounts of said acrylic polymer crosslinked with divinyl glycol and/or said polymers derived from acrylic acid crosslinked with allyl sucrose or allyl pentaerythritol are individually comprised between 0.05 and 5% by weight of the formulation.

20. The method according to claim 1, wherein the dose of estriol is less than or equal to 0.1 mg/day.

21. The method according to claim 14, wherein the dose of estriol is between 0.01 and 0.05 mg/day.

22. A method of prevention and/or treatment of urogenital atrophy due to estrogen deficiency in women who suffer or have suffered from an estrogen-dependent tumor or are carrier of genetic mutations BRCA1 or BRCA2; wherein the method comprises vaginally administering a pharmaceutical estriol formulation capable of self-limiting absorption of estriol, wherein the pharmaceutical formulation is administered in a dose of estriol less than or equal to 0.3 mg/day; and wherein the method at the same time achieves preventing or very significantly decreasing the risk associated with estrogen therapy of stimulating the development of estrogen-dependent tumors at systemic level.

23. The method according to claim 22, wherein the pharmaceutical formulation is administered in once daily doses for at least 2 or 3 weeks.

* * * * *

UNITED STATES PATENT AND TRADEMARK OFFICE
CERTIFICATE OF CORRECTION

Page 1 of 1

PATENT NO.         : 9,114,143 B2
APPLICATION NO.    : 13/057775
DATED              : August 25, 2015
INVENTOR(S)        : Acebrón Fernández et al.

It is certified that error appears in the above-identified patent and that said Letters Patent is hereby corrected as shown below:

On the Title page, please add item (30) the Foreign Application Priority Data:

August 2, 2008 (ES) ...........................P200802384

Signed and Sealed this
Fifteenth Day of March, 2016

Michelle K. Lee
*Director of the United States Patent and Trademark Office*